(12) United States Patent
Traeger et al.

(10) Patent No.: US 10,842,961 B2
(45) Date of Patent: Nov. 24, 2020

(54) ARRANGEMENT IN THE FORM OF A TRACHEOSTOMA PROSTHESIS FOR EASY INSERTION AND EASY REMOVAL OF AN INNER CANNULA

(71) Applicant: Primed Halberstadt Medizintechnik GmbH, Halberstadt (DE)

(72) Inventors: Peter Traeger, Halberstadt (DE); Klaus Klimenta, Zilly (DE)

(73) Assignee: Primed Halberstadt Medizintechnik GmbH, Halberstadt (DE)

( * ) Notice: Subject to any disclaimer, the term of this patent is extended or adjusted under 35 U.S.C. 154(b) by 229 days.

(21) Appl. No.: 16/230,119

(22) Filed: Dec. 21, 2018

(65) Prior Publication Data

US 2019/0143062 A1 May 16, 2019

Related U.S. Application Data

(63) Continuation-in-part of application No. 14/363,176, filed as application No. PCT/DE2012/001182 on Nov. 29, 2012, now abandoned.

(30) Foreign Application Priority Data

Dec. 5, 2011 (DE) .................. 10 2011 120 694

(51) Int. Cl.
*A61M 16/04* (2006.01)
*A61M 16/08* (2006.01)
(52) U.S. Cl.
CPC .... *A61M 16/0427* (2014.02); *A61M 16/0465* (2013.01); *A61M 16/0816* (2013.01); *A61M 2205/0216* (2013.01)

(58) Field of Classification Search
CPC .......... A61M 16/0427; A61M 16/0497; A61M 16/0465; A61M 16/0816; A61M 2205/0216
USPC .......... 128/207.14–17, 200.26; 604/158, 165
See application file for complete search history.

(56) References Cited

U.S. PATENT DOCUMENTS

| | | |
|---|---|---|
| 4,270,529 A | 6/1981 | Muto |
| 4,632,108 A | 12/1986 | Geil |
| 4,817,598 A | 4/1989 | LaBombard |
| 2005/0166924 A1 | 8/2005 | Thomas |
| 2008/0072911 A1* | 3/2008 | Flagler .............. A61M 16/0057 128/207.14 |

(Continued)

FOREIGN PATENT DOCUMENTS

| | | |
|---|---|---|
| DE | 3819237 | 12/1988 |
| DE | 19514433 | 1/1996 |

(Continued)

*Primary Examiner* — Timothy A Stanis
*Assistant Examiner* — Victoria Murphy
(74) *Attorney, Agent, or Firm* — Norris McLaughlin, P.A.

(57) ABSTRACT

A tracheostoma prosthesis having inner and outer cannulas is provided with a lockable connection for releasably locking the inner cannula to the outer cannula under the influence only of compressive force for locking and tensile force for unlocking. Surfaces on a proximal part of the inner cannula for gripping by a thumb and forefinger are exposed by recesses provided in a proximal part of the outer cannula. These surfaces permit manual application of sufficient compressive and tensile force to respectively lock and unlock the lockable connection.

3 Claims, 3 Drawing Sheets

(56) References Cited

U.S. PATENT DOCUMENTS

2014/0360495 A1* 12/2014 Traeger ............ A61M 16/0427
                                                  128/200.26

FOREIGN PATENT DOCUMENTS

DE    202004020109    3/2005
GB           634978   3/1950

* cited by examiner

ARRANGEMENT IN THE FORM OF A TRACHEOSTOMA PROSTHESIS FOR EASY INSERTION AND EASY REMOVAL OF AN INNER CANNULA

REFERENCE TO RELATED APPLICATION

This is a continuation-in-part application of application Ser. No. 14/363,176, filed Jun. 10, 2014, which is currently pending.

BACKGROUND OF THE INVENTION

The invention relates to an arrangement in the form of a tracheostoma prosthesis for the easy insertion and easy removal of an inner cannula.

Tracheostoma prostheses (also known as tracheostomy cannulas, tracheal cannulas, endotracheal tubes or tracheostomy tubes) for treating tracheostomized or laryngectomized patients with open throat (so called tracheostoma) have been known for decades.

From DE 195 14 433 A1 a tracheostomy cannula is known that is to be inserted in a tracheostoma and consists of a tubular outer cannula with a cannula shield and of a tubular inner cannula which can be guided into the outer cannula and locked with it at the proximal part.

This lock has the disadvantage that it can be possibly jammed and then it is difficult to release it so that the removal of the inner cannula from the outer cannula is considerably more complicated.

DE 38 19 237 A1 discloses an endotracheal tube comprising an outer tube and an inner tube and the inner tube is provided with a locking element for a snap-lock connection with the outer tube. The inner tube is also provided with an easily accessible operating handle which is connected with the locking element and to be used to pull out the inner tube from the connection with the outer tube.

This loop- or bracket-shaped operating handle has the disadvantage that it will tear off the inner tube, if the tensile forces are too high during the removal of the inner tube from the outer tube (e.g. if the inner tube is clamped in the outer tube or it is bonded by body secretions or the system is improperly handled) so that as a result of this tearing the inner tube can only be removed with very great effort from the outer tube. The design patent 40208362-0001 and its description is related to a push-button connection for a treacheal cannula consisting of a six-teeth, round plastic part at the inner cannula and a round bead-like edge at the outer cannula. The inner cannula is released from the push-button connection with the outer cannula by levering the push-button connection. This is done by positioning the thumb and index finger laterally at the push-button connection and levering it out of the outer cannula. In order to fix the inner cannula in the outer cannula, the inner cannula is gently pressed on the push-button connection after inserting it in the outer cannula. It snaps into place with an audible click.

This push-button connection has the disadvantage that the inner cannula must be removed from the outer cannula by levering the push-button connection which is done by positioning the thumb and index finger laterally and then releasing said connection. When using the thumb and index finger for positioning them at the connection and subsequently levering it, the nails of these fingers can be injured so that the handling of this push-button connection can be very awkward.

DE 202004 020 109 U1 discloses a treacheostoma tube with an adapter for laryngectomy consisting of a tracheostoma tube equipped with an adapter at its distal end, and the free end of this adapter is provided with one recess or two oppositely arranged recesses at its edge. The adapter is used to add accessory parts (such as Trachi-Naze® (registered trademark of Kapitex Healthcare)) to a tracheostoma tube from the outside by coupling these accessory parts to the tracheostoma tube in a form-locked manner. The accessory parts can be very easily released from the adapter again by putting one finger of one hand into the recess or the thumb and index finger of one hand into the two recesses.

However, this technical solution has the disadvantage that it is not possible to insert an inner cannula in the outer cannula.

SUMMARY OF THE INVENTION

The object of the invention is to provide an arrangement in the form of a tracheostoma prosthesis for the easy insertion and easy removal of an inner cannula, which arrangement avoids the disadvantages of prior art and in particular allows to pull out the inner cannula from a locked connection to the outer cannula with minimal effort by using the thumb and index finger.

According to the invention, there is provided a tracheostoma prosthesis that comprises an outer cannula and an inner cannula which can be inserted in this outer cannula, and a proximal end region of the proximal part of the outer cannula is provided with two oppositely arranged recesses configured receive a thumb and index finger of a hand for gripping the proximal end region of the inner cannula at surfaces thereof exposed by the recesses. The recesses may be arcuate, for example circular arcuate.

In further accordance with the invention, there is provided a lockable connection between the tubular inner and outer cannulas. The outer cannula has a proximal part and a distal part, the distal part being configured to be received in a trachea through a tracheastoma. A cannula shield is fixed to the outer cannula at a distal end of the proximal part. The inner cannula has a proximal part and a distal part and is received in the outer cannula through an opening in the outer cannula at a proximal end of the proximal part of the outer cannula. At least the proximal part of each of the inner and outer cannula is made of a material which is flexible and resilient. Preferred such materials are flexible and resilient plastics. Examples of such plastics are PVC, silicone and thermoplastic polyurethanes. The lockable connection between the inner and outer cannulas comprises interacting radially projecting structures of the respective proximal parts together with a radially outwardly extending bead surrounding the opening at the proximal end of the inner cannula. The aforementioned gripping recesses cooperate with the lockable connection in the sense that sufficient compressive and tensile force can be applied to the proximal part of the inner cannula while gripping the proximal part of the inner cannula with a thumb and forefinger at the surfaces exposed by the recesses to, respectively, lock and unlock the lockable connection. Moreover, the bead serves two functions, namely, as part of the lockable connection between the inner and outer cannulas, as described below, and, secondly, because the bead abuts the surfaces to be gripped exposed by the recesses, when tensile force is applied by the thumb and forefinger, the bead, which contacts the thumb and forefinger, provides resistance against slippage of the thumb and forefinger.

The lockable connection comprises a first radially extending annular projection comprising an interior part of the proximal part of the outer cannula, a second radially extending annular projection comprising an exterior part of the proximal part of the inner cannula, and the bead. The first and second radially extending annular projections are configured so that: (a) for locking the inner cannula in the outer cannula, a distal surface of the first radially extending annular projection is brought into engagement with a proximal surface of the second radially extending annular projection and a distal surface of the bead is brought into abutment with a proximal end surface of the proximal part of the outer cannula by inserting the inner cannula into the outer cannula, gripping the inner cannula by a thumb and index finger of a hand at surfaces of the proximal part of the inner cannula exposed by the recesses and, with the hand gripping the proximal part of the inner cannula in this manner, applying compressive force to the inner cannula in an axial direction of the proximal parts of the inner and outer cannulas; and (b) for unlocking the inner cannula from the outer cannula, the inner cannula is gripped by a thumb and index finger of the hand at surfaces of the proximal part of the inner cannula exposed by the recesses and the hand gripping the proximal part of the inner cannula in this manner applies tensile force to the inner cannula in an axial direction of the proximal parts of the inner and outer cannulas whereby, under influence of the tensile force and the flexibility and resilience of the materials of which the respective proximal parts of the inner and outer cannulas are made, the second projection slides over the first projection toward the proximal end of the outer cannula, disengaging the distal surface of the first radially extending annular projection from the proximal surface of the second radially extending annular projection.

BRIEF DESCRIPTION OF THE DRAWINGS

In the following, the invention is explained in more detail by means of drawings. They show.

DETAILED DESCRIPTION OF THE INVENTION

Figure 1:
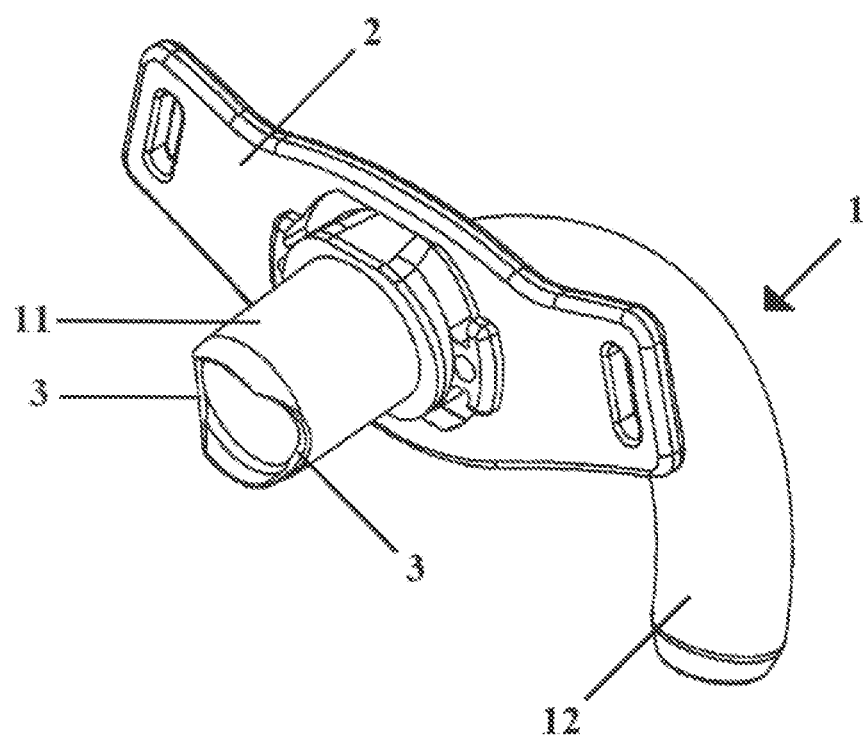
FIG. 1 is a schematic overview drawing of an embodiment of an outer cannula of the inventive arrangement.
Figure 2:
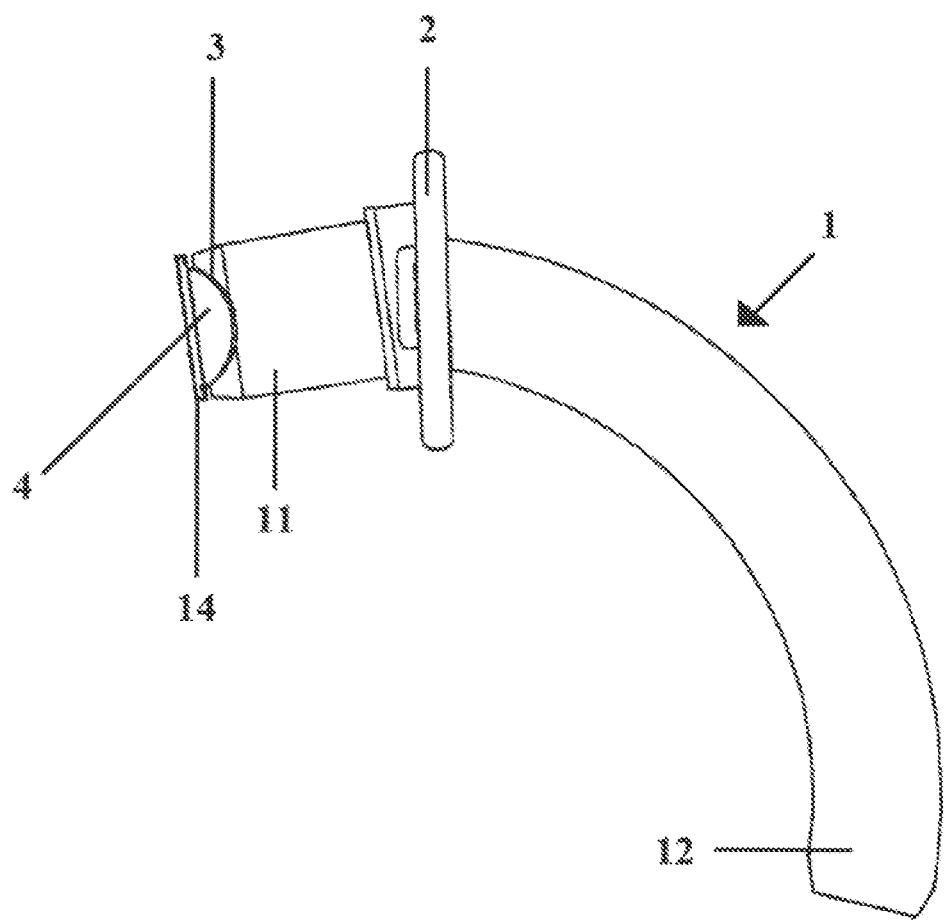
FIG. 2 is a lateral view of an embodiment of the inventive arrangement with an outer cannula and an inner cannula.

The outer cannula (1) shown in FIGS. 1 and 2 has a tubular configuration according to the state of the art and is provided with a proximal part (11) and a distal part (12).

The inner cannula (4) shown in FIG. 2 has also a tubular configuration and is provided with a radially outwardly extending bead (14) which surrounds the opening at the proximal end of the inner cannula.

The inner cannula (4) is inserted in the opening at the proximal part (11) of the outer cannula (1) and can be locked in the proximal part (11) of the tubular outer cannula (1) by a lockable connection described below.

According to the state of the art, the tubular outer cannula (1) is provided with a cannula shield (2) at its proximal part (11).

A proximal end region of the proximal part (11) of the outer cannula (1) is provided with two circular-arc shaped, recesses (3) positioned opposite to each other, typically about 180° apart configured to be gripped by thumb and index finger.

These recesses (3) and the bead (14) have the advantage that an inner cannula (4) locked in the outer cannula (1) according to the invention can be easily and without any difficulty—even with strong tensile forces—removed from the outer cannula (1) by the direct gripping of thumb and index finger at surfaces in a proximal end region of the proximal part (16) (see FIG. 3) of the inner cannula (4) with the proximal part (16) being exposed in the areas of the recesses (3). When doing this, neither the nails of thumb and index finger are damaged nor components of the inner cannula.

Thus, the thumb and index finger grip in a very ergonomic manner in the area of the recesses (3) so that the tensile or compressive forces applied by the thumb and index finger in the axial direction of the proximal parts (11) and (16) can be optimally transmitted to the inner cannula (4) to unlock it from the outer cannula (1) or lock it to the inner cannula, respectively, provided that locking and unlocking is provided by the means described below.

According to the state of the art, the outer cannula (1) and the inner cannula (4) can be configured as a standard arc from 80° to 110°.

Figure 3:
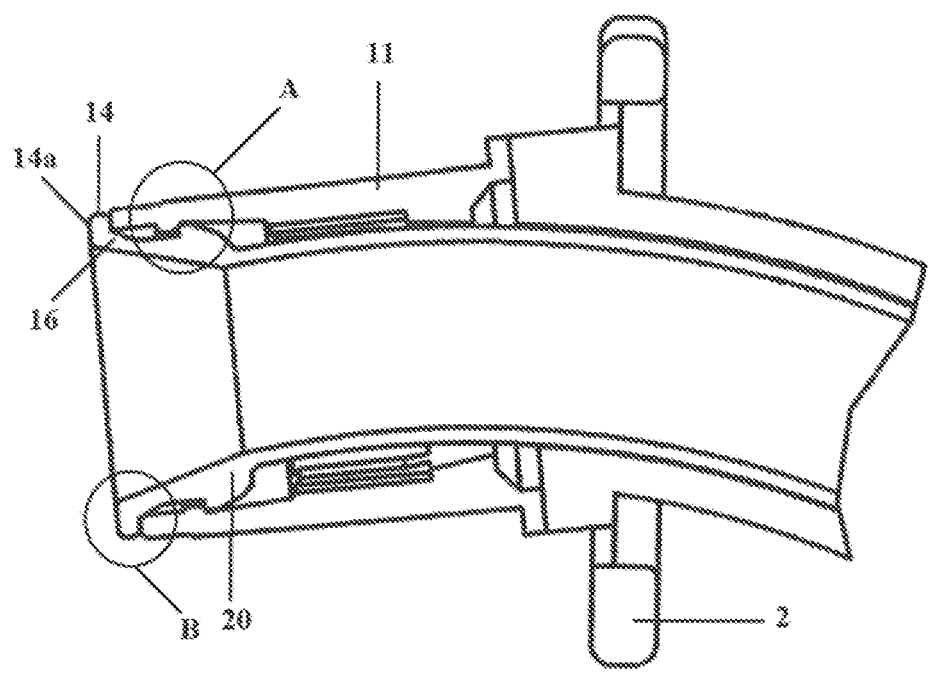
FIG. 3 is an axial cross-section of an embodiment of the invention, including the proximal end parts of the inner and outer cannulas in the locked configuration.
Figures 3A, 3B:
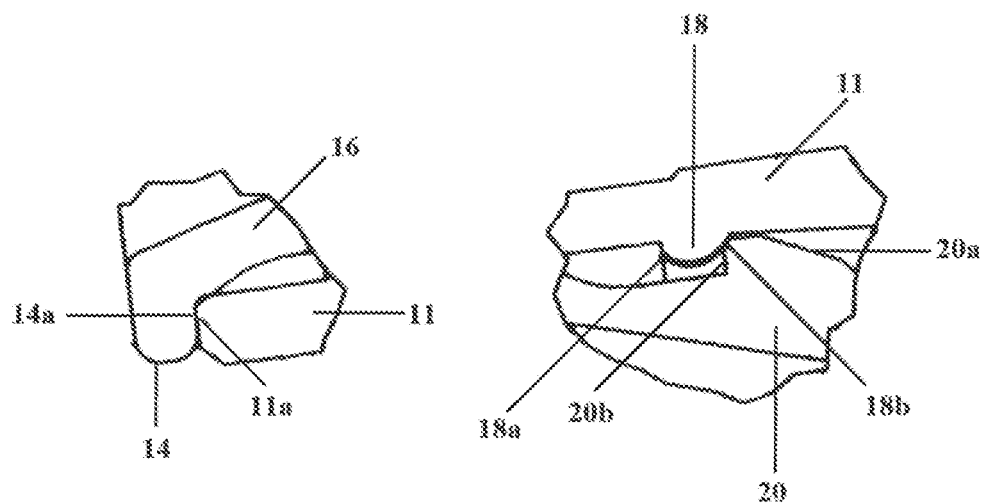
FIGS. 3A and 3B are enlargements of portions of FIG. 3 designated A and B.

The lockable connection between the inner cannula (4) and the outer cannula (1) is shown in FIGS. 3, 3A and 3B in the locked configuration. The proximal part (11) includes at the interior thereof a radially extending annular projection (18). The proximal part (16) includes at the exterior thereof a radially extending annular projection (20). When the inner cannula (16) is inserted in the outer cannula (14), the inclined surface (20a) of the projection (20) abuts against a proximal surface (18a) of the projection (18). Then, compressive force in the axial direction of the proximal parts (11) and (16) is applied by the thumb and forefinger gripping the surfaces exposed by the recesses (3), and the projection (20) slides over the projection (18) so that the proximal surface (20b) of the projection (20) abuts the distal surface (18b) of the projection (18). This is facilitated by the flexibility and resilience of the materials of which the proximal parts (11) and (16), including projections (18) and (20), are made as well as by the inclination of the surface (20a). The lockable connection is further configured so that when the proximal surface (20b) of the projection (20) abuts the distal surface (18b) of the projection (18), the proximal end surface (11a) of the proximal part (11) abuts the distal surface (14a) of the bead (14). Thereby, the proximal parts (11) and (16) are locked together so they cannot move axially relative to each other. To unlock the connection, the surfaces of the proximal part (16) exposed by the recesses (3) are gripped by a thumb and forefinger of the hand and tensile force is applied by the thumb and forefinger in the axial direction of the proximal parts (11) and (16). Under the influence of the applied tensile force, and aided by the aforementioned flexibility and resilience of the materials, the projection (20) slides over the projection (18), releasing the inner cannula (4) from its locked connection to the outer cannula (1).

The hereinabove embodiment is exemplary and is not necessarily is intended to limit the scope of the invention.

The invention claimed is:
1. A tracheastoma prosthesis comprising:
    a tubular outer cannula having a proximal part made of a flexible and resilient material and a distal part, the distal part being configured to be received in a trachea through a tracheastoma, a cannula shield fixed to the outer cannula at a distal end of the proximal part, and a tubular inner cannula having a proximal part made of a flexible and resilient material and a distal part and being received in the outer cannula through an opening in the outer cannula at a is proximal end of the proximal part of the outer cannula and being lockable in the outer cannula by a lockable connection of a proximal end of the inner cannula to the proximal end of the outer cannula, the inner cannula, at its proximal end, having an opening and a radially outwardly extending bead surrounding the opening, wherein a proximal end region of the proximal part of the outer cannula abutting the bead is provided with two recesses arranged opposite each other and configured to receive a thumb and index finger of a hand for gripping the proximal end of the inner cannula at surfaces thereof exposed by the recesses, and the lockable connection comprises a first radially extending annular projection comprising an interior part of the proximal part of the outer cannula, a second radially extending annular projection comprising an exterior part of the proximal part of the inner cannula, and the bead, the first and the second radially extending annular projections being configured so that, for locking the inner cannula in the outer cannula, a distal surface of the first radially extending annular projection is brought into engagement with a proximal surface of the second radially extending annular projection and a distal surface of the bead is brought into abutment with a proximal end surface of the proximal part of the outer cannula by inserting the inner cannula into the outer cannula, gripping the inner cannula by the thumb and the index finger of the hand at the surfaces of the proximal part of the inner cannula exposed by the recesses and, with the hand gripping the proximal part of the inner cannula in this manner, applying compressive force to the inner cannula in an axial direction relative to the proximal parts of the inner and the outer cannulas and, for unlocking the inner cannula from the outer cannula the tracheastoma prosthesis is configured such that the inner cannula is gripped by the thumb and the index finger of the hand at the surfaces of the proximal part of the inner cannula exposed by the recesses and the hand gripping the proximal part of the inner cannula in this manner applies tensile force to the inner cannula in an axial direction relative to the proximal parts of the inner and the outer cannulas whereby, under influence of the tensile force and the flexibility and the resilience of the materials of which the respective proximal parts of the inner and the outer cannulas are made, the second radially extending annular projection is configured to slide over the first radially extending annular projection toward the proximal end of the outer cannula, disengaging the distal surface of the first radially extending annular projection from the proximal surface of the second radially extending annular projection.

2. The tracheastoma prosthesis according to claim 1, wherein the flexible and resilient material of the outer cannular and/or the inner cannula is a plastic.

3. The tracheastoma prosthesis according to claim 2, wherein the plastic is a flexible and resilient PVC, silicone or thermoplastic polyurethane.

\* \* \* \* \*